US010493267B2

(12) United States Patent
Greenberg et al.

(10) Patent No.: US 10,493,267 B2
(45) Date of Patent: Dec. 3, 2019

(54) ELECTRODE ARRAYS FOR A VISUAL PROSTHESIS

(71) Applicant: Second Sight Medical Products, Inc., Sylmar, CA (US)

(72) Inventors: Robert Greenberg, Los Angeles, CA (US); Neil Talbot, La Crescenta, CA (US); Jerry Ok, Canyon Country, CA (US); Proyag Datta, Castaic, CA (US); Andrew Sha, Arleta, CA (US); Brianna Thielen, North Hollywood, CA (US); Dustin Tobey, Glendora, CA (US); Deborah Sigel, Tujunga, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 95 days.

(21) Appl. No.: 15/374,931

(22) Filed: Dec. 9, 2016

(65) Prior Publication Data

US 2017/0165476 A1    Jun. 15, 2017

Related U.S. Application Data

(60) Provisional application No. 62/266,513, filed on Dec. 11, 2015.

(51) Int. Cl.
*A61N 1/05* (2006.01)
*A61N 1/36* (2006.01)

(52) U.S. Cl.
CPC ....... *A61N 1/0543* (2013.01); *A61N 1/36046* (2013.01)

(58) Field of Classification Search
None
See application file for complete search history.

(56) References Cited

U.S. PATENT DOCUMENTS

| | | | |
|---|---|---|---|
| 4,628,933 A | 3/1986 | Michelson | |
| 4,573,481 A | 12/1986 | Bullara | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,912,556 B2 * | 3/2011 | Greenberg | A61N 1/0558 607/116 |
| 8,145,332 B2 | 3/2012 | Yao et al. | |
| 8,150,534 B2 * | 4/2012 | Greenberg | A61N 1/0558 607/116 |
| 8,396,562 B2 | 3/2013 | Ameri et al. | |

(Continued)

FOREIGN PATENT DOCUMENTS

| | | |
|---|---|---|
| WO | WO2008101225 | 8/2008 |
| WO | WO2009003182 | 12/2008 |

*Primary Examiner* — Ankit D Tejani
(74) *Attorney, Agent, or Firm* — Scott Dunbar

(57) ABSTRACT

Electrode arrays for biological implants are disclosed, particularly for stimulating a retina. The present disclosure provides array for improving apposition (reducing the space between the array and the retina. The present disclosure also provides electrode array designs that can be made approximately spherical to increase the field of view of a visual prosthesis while still maintaining good apposition.

5 Claims, 12 Drawing Sheets

(56) References Cited

U.S. PATENT DOCUMENTS

| | | | | |
|---|---|---|---|---|
| 8,588,937 B2* | 11/2013 | Greenberg | ............ | A61N 1/0558 607/116 |
| 2008/0288037 A1 | 11/2008 | Neysmith et al. | | |
| 2009/0228086 A1* | 9/2009 | Greenberg | ............ | A61N 1/0543 607/116 |
| 2011/0144731 A1* | 6/2011 | Greenberg | ............ | A61N 1/0543 607/116 |
| 2012/0296444 A1* | 11/2012 | Greenberg | ............ | A61B 5/4064 623/25 |
| 2013/0030508 A1* | 1/2013 | Greenberg | ............ | A61N 1/0543 607/116 |
| 2015/0157862 A1* | 6/2015 | Greenberg | ............ | A61B 5/6868 607/60 |

* cited by examiner

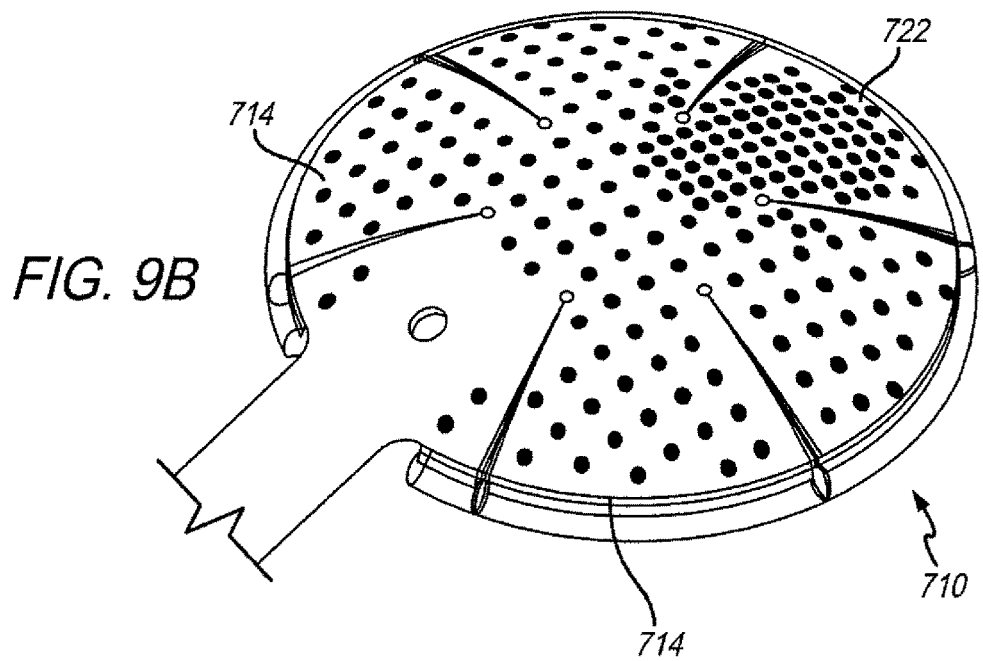

ELECTRODE ARRAYS FOR A VISUAL PROSTHESIS

TECHNICAL FIELD

The present disclosure relates to neural implants, particularly visual prostheses. More particularly, it relates to electrode arrays and their leads for use in visual prostheses for stimulating a retina.

SUMMARY

Electrode arrays for biological implants are disclosed, particularly for stimulating a retina. The present disclosure provides array designs for improving apposition (reducing the space between the electrodes and the retina). The present disclosure also provides electrode array designs that can be made approximately spherical to increase the field of view of a visual prosthesis while still maintaining good apposition.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 9B shows the electrode array of FIG. 9A curved as it would be on the retina.

DETAILED DESCRIPTION

Biological implants, such as ocular implants to be attached to the human retina or other neural interface devices, often comprise a set of electronic components which may control and monitor the function of the implant, and the neural interfacing component itself, usually an array of electrodes. While described here in terms of an electrode array to be attached to the retina for a visual prosthesis, the present disclosure may also be applicable for an electrode array to attached to the visual cortex for a visual prosthesis, a spinal cord stimulator, a deep brain stimulator, a cortical or peripheral nerve interface (stimulator or recorder) for a motor prosthesis, or a wide range of other neural interface devices. Electrode arrays benefit from both being flexible to conform to the target tissue, and from being pre-formed to approximate that target tissue.

Figure 1:
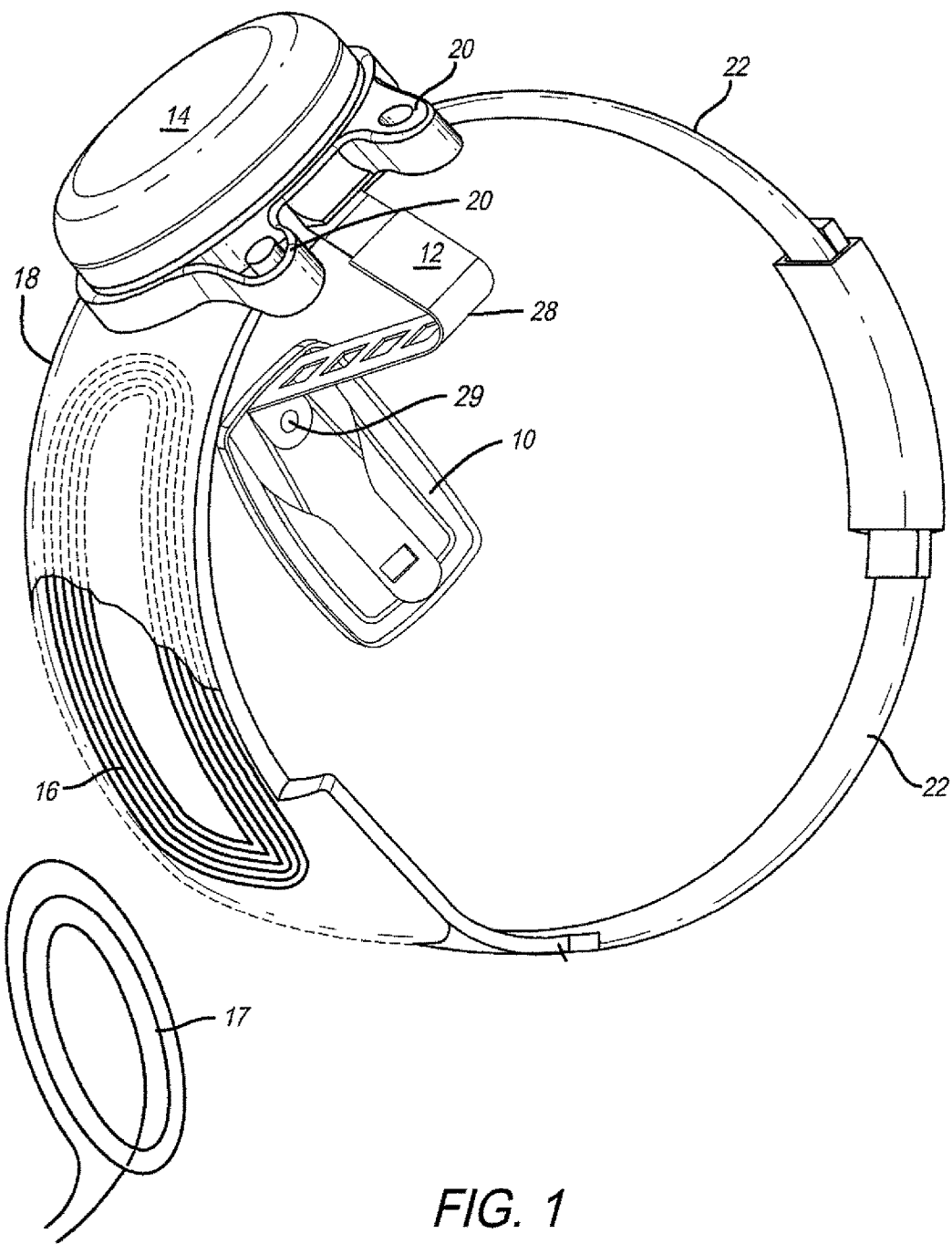
FIG. 1 shows an overview of the implantable portion of a visual prosthesis.

FIG. 1A shows a perspective view of the implanted portion of a visual prosthesis. A flexible circuit includes a flexible circuit electrode array 10 which is mounted by a retinal tack (not shown) through tack opening 29, or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the secondary inductive coil 16 and electronics package 14 in an end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
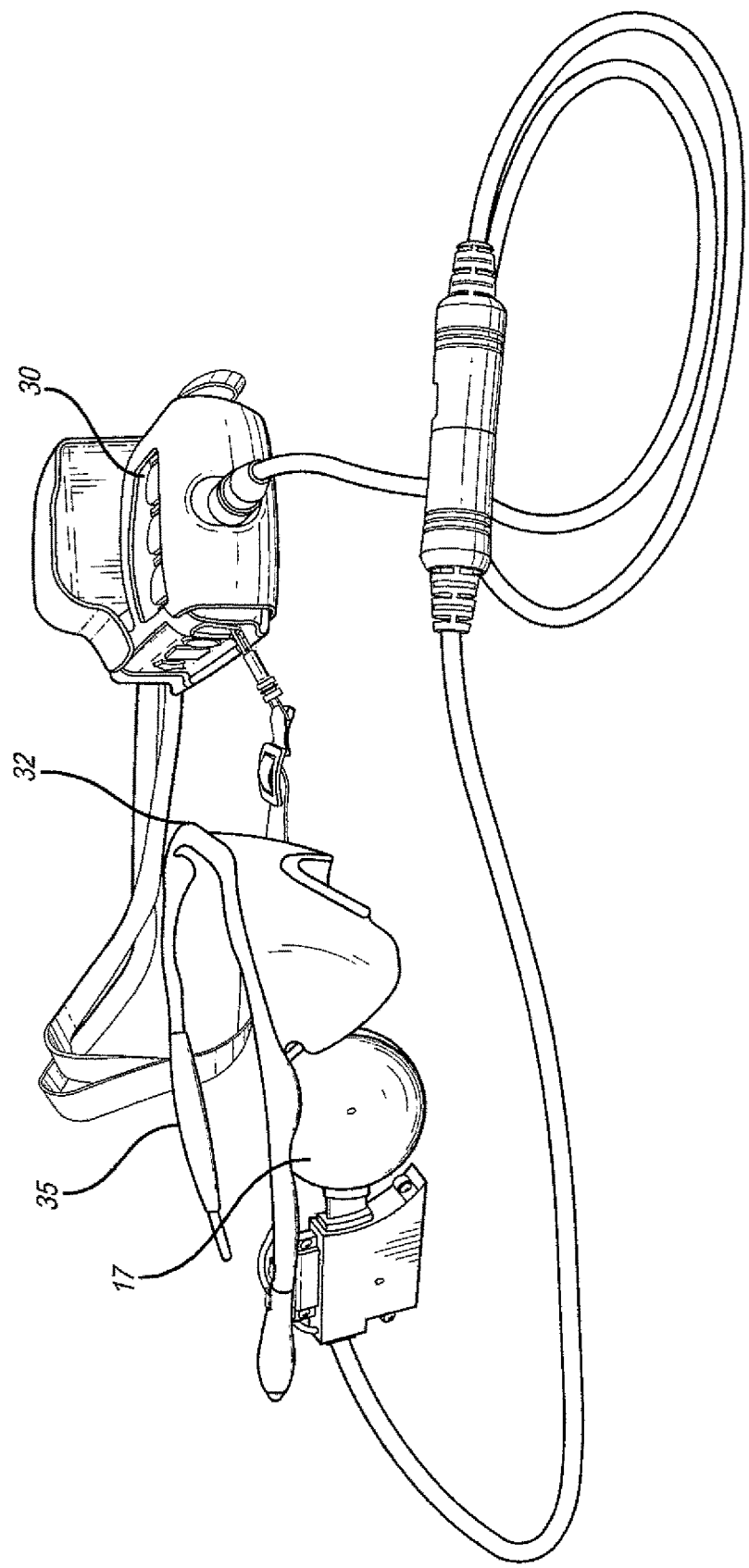
FIG. 2 shows an overview of the external portion of a visual prosthesis.

Referring to FIG. 2, a video camera 32, on the glasses 35, captures a video image that is sent to a video processing unit (VPU) 30. The VPU 30 processes the image from the camera 32 and transforms it into electrical stimulation patterns that are transmitted to the external coil 17. The external coil 17 sends the electrical stimulation patterns and power via radio-frequency (RF) telemetry to the implanted retinal stimulation system. The internal coil 16 of the retinal stimulation system receives the RF commands from the external coil 17 and transmits them to the electronics package 14 that in turn delivers stimulation to the retina via the electrode array 10. Additionally, the retinal stimulation system may communicate safety and operational status back to the VPU 30 by transmitting RF telemetry from the internal coil 16 to the external coil 17. Separate coils for transmitting and receiving may also be used. The visual prosthesis apparatus may be configured to electrically activate the retinal stimulation system only when it is powered by the VPU 30 through the external coil 17.

Figure 3:
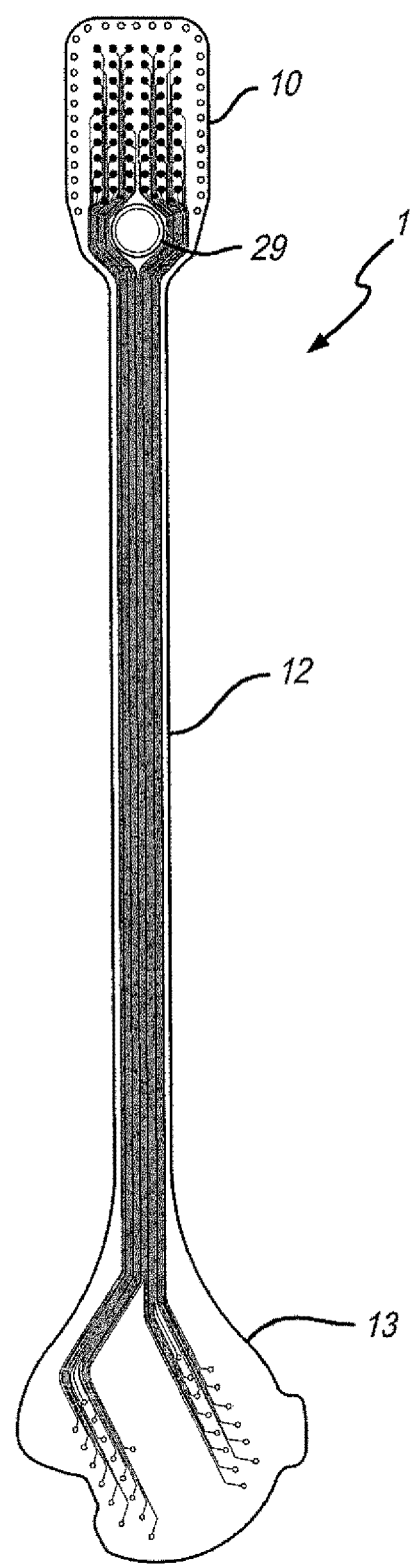
FIG. 3 shows a flexible circuit electrode array with the bond pad at one end, electrodes at the other end and traces connecting the bond pads with electrodes.

Referring to FIG. 3, the flexible circuit 1 is preferably a sandwiched polymer body with the electrode array 10 at one end bond pads 13 for connecting the array to the electronics package 14 at the other end, and traces through a cable 12 connecting bond pads to electrodes. Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating or casting. A layer of metal, preferably platinum, is applied to the polymer and patterned to create electrodes bond pads and leads connecting electrodes to bond pads. Patterning is commonly done by photolithographic methods. A second layer of polymer is applied over the metal layer and patterned to leave openings for the electrodes, or openings are created later by means such as laser ablation. Hence the array 10, its supply cable 12 and bond pads 13 are formed of a single body. Additionally, multiple alternating layers of metal and polymer may be applied to obtain more metal traces within a given width.

The pressure applied against the retina, or other neural tissue, by an electrode array is critical. Too little pressure causes increased electrical resistance between the array and retina, along with electric field dispersion. Too much pressure may block blood flow causing retinal ischemia and hemorrhage. Pressure on the neural retina may also block axonal flow or cause neuronal atrophy leading to optic atrophy. Common flexible circuit fabrication techniques such as photolithography generally require that a flexible circuit electrode array be made flat. Since the retina is approximately spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

It is further advantageous to make a thinner polyimide array as the core layer and coat the entire array with a thin layer of Polydimethylsiloxane (PDMS) and to open up the electrode sites and for plating the electrodes with Pt gray or other metal electrode materials.

The electrode array 10 comprises a number of electrical traces which may follow different pattern designs. In one embodiment, the electrical traces run on multiple layers on top of one another. For example, a layer of electrical traces may follow a certain arrangement, and a second layer of electrical traces have its own arrangement, with the two layers being separated by a thin layer of dielectric material so as to achieve electrical insulation.

Figure 4A:
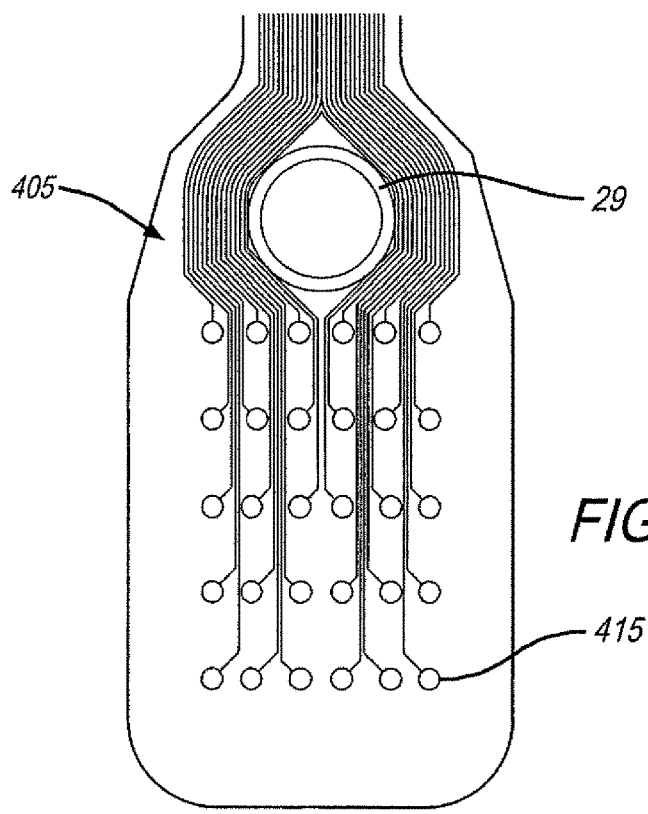
FIG. 4A shows a first layer of traces and electrodes in a flexible circuit electrode array.
Figure 4B:
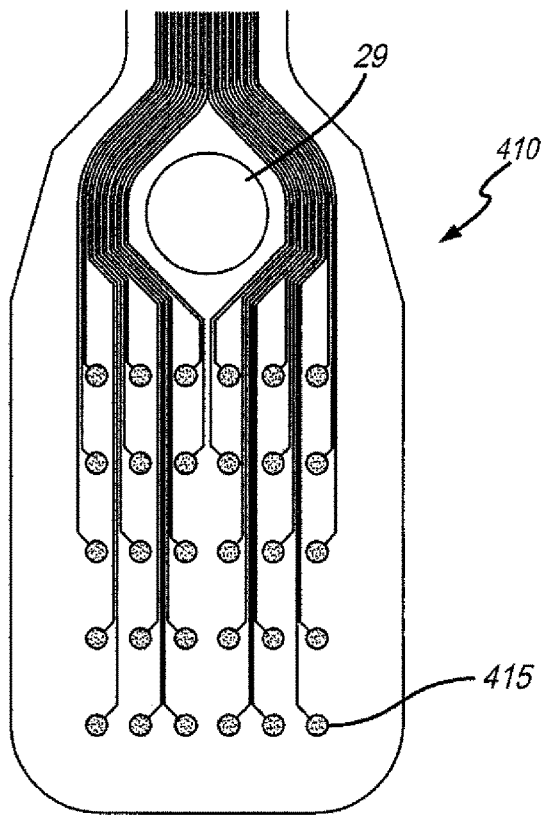
FIG. 4B shows a second layer of traces and electrodes in a flexible circuit electrode array.

In a preferred embodiment, an array may contain 60 thin platinum traces that connect the electrodes to the bond pads. Referring to FIGS. 4A and 4B, half (i.e., 30) of the traces are on one layer of polyimide 405 and the other half on a second layer of polyimide 410. Each trace in FIGS. 4A and 4B connects to one circular electrode 415.

Figure 5A:
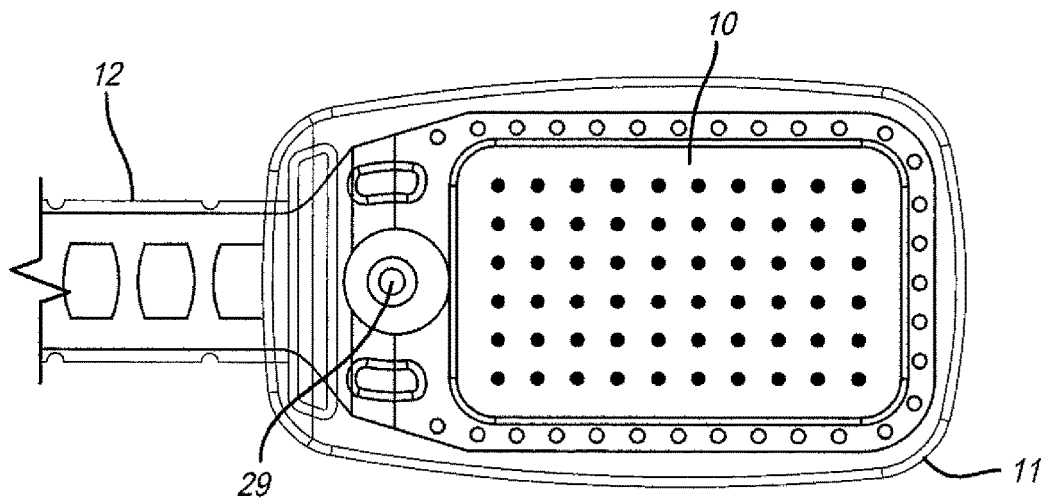
FIG. 5A shows a prior art electrode array.
Figure 5B:
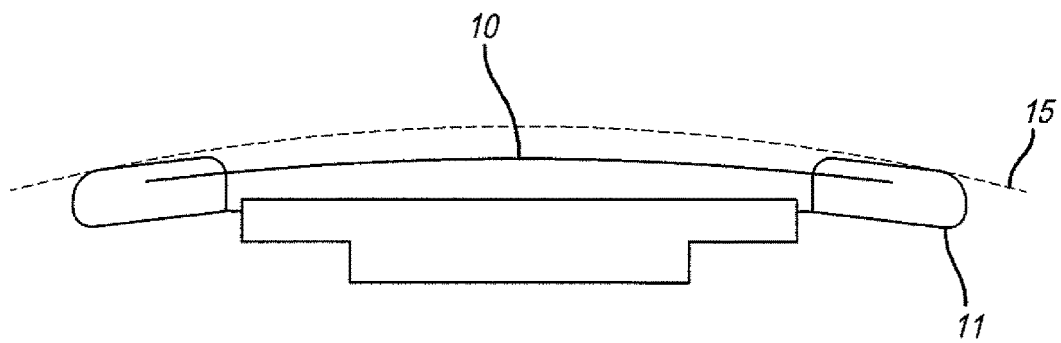
FIG. 5B shows the prior art electrode array as attached to a retina.

FIGS. 5A and 5B represent the existing state of the art. A polyimide flexible circuit includes an electrode array 10 and connected cable 12. The electrode array 10 portion of the polyimide flexible circuit is encased in a PDMS coating 11. When placed against a retina 15, the PDMS coating 11 protects the retina 15 from the sharp edges of the polyimide. However, the PDMS coating 11 creates a gap between the electrodes in the electrode array 10 and the retina 15.

Figure 6A:
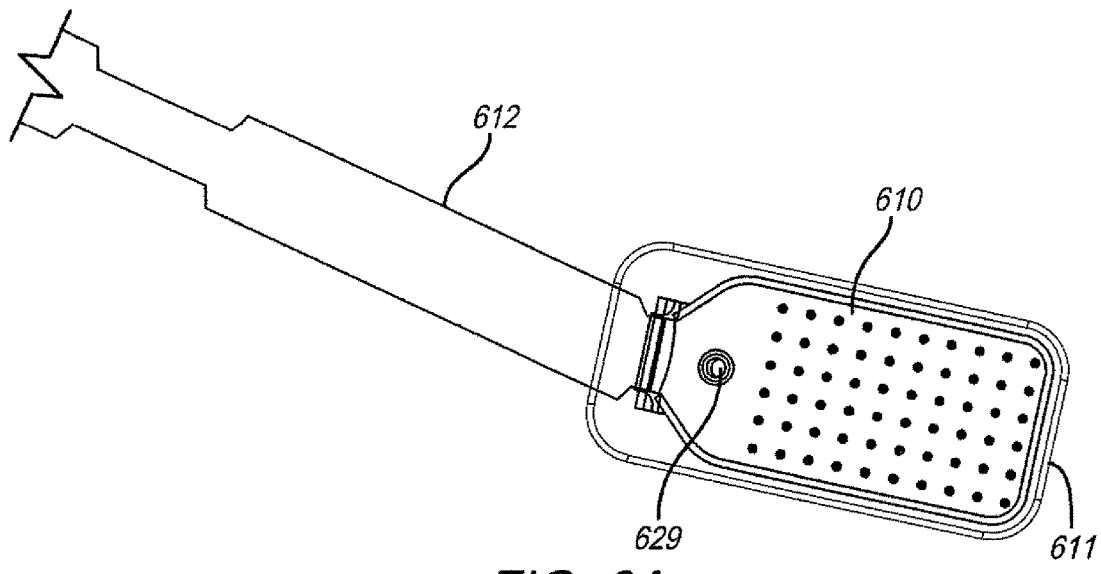
FIG. 6A shows a flexible circuit electrode array design where the flexible circuit is curved out at its edges and embedded in silicone to allow it to remain flush with a retina.
Figure 6B:
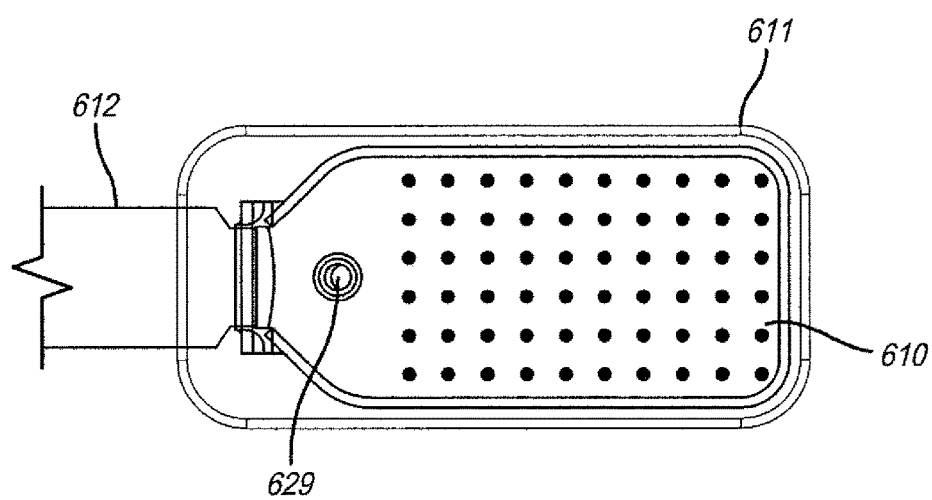
FIG. 6B shows the electrode array portion of the flexible circuit electrode array of FIG. 6A.
Figure 6C:
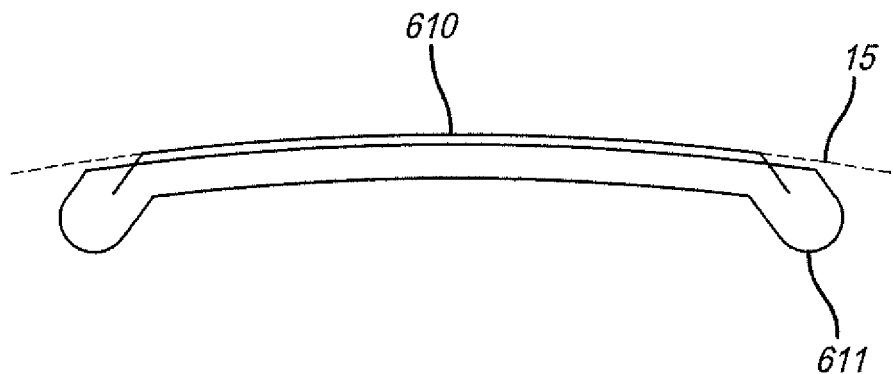
FIG. 6C shows the electrode array of FIGS. 6A and 6B as attached to a retina.
Figure 6D:
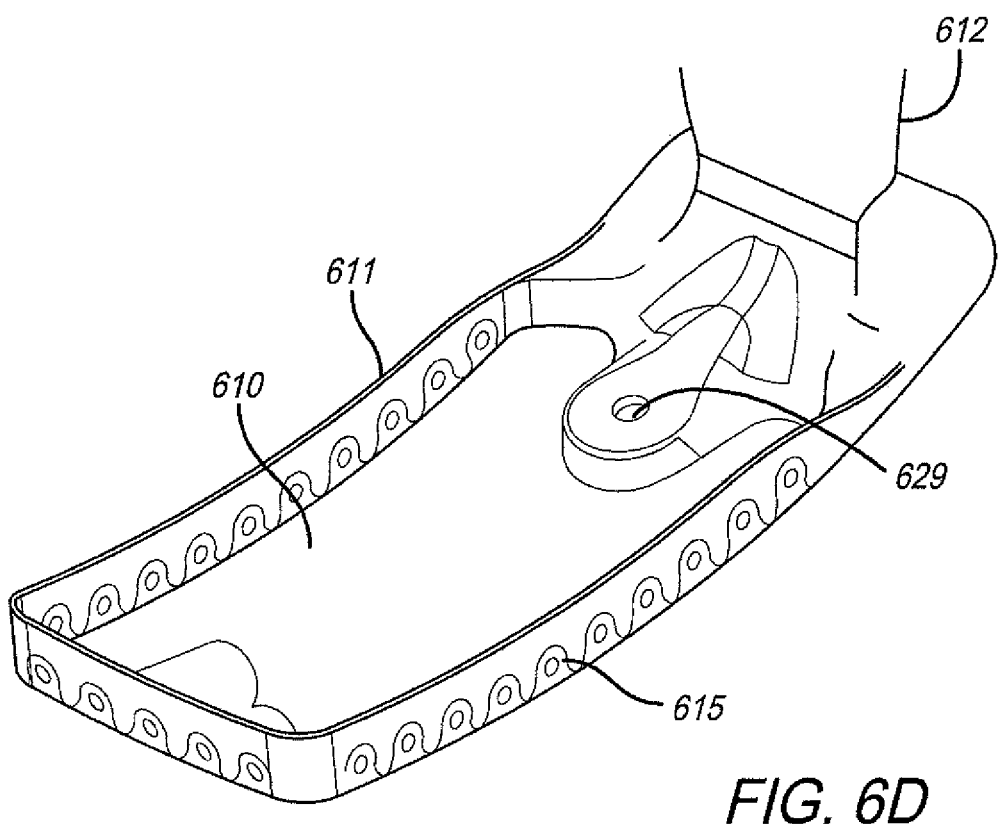
FIG. 6D shows the electrode array of FIG. 6A through 6C, in particular, how the array is curved out at its edges.

FIGS. 6A through 6D show an improved electrode array with curved edges. This design decreases the overall size of the electrode array without decreasing the size of the electrode field. This design uses a flexible circuit as shown in FIG. 3, including an electrode array 610 and cable 612. The flexible circuit electrode array 610 is curved up at is edges through thermoforming and over molded in that position by the PDMS coating 611. The array is tacked to the retina with a tack (not shown) through the tack opening 629. As can be seen in FIG. 6C, curving the flexible circuit electrode array 610 up at its edges, both decreases the overall size and allows the flexible circuit electrode array 610 to lay flat against the retina 15. It should be noted that the figures are not drawn to scale. This figure, along with FIG. 5B, in particular accentuate the thickness of the silicone so it can be seen. In the preferred embodiment, the flexible circuit is polyimide about 12 µm thick. The polymer over-mold is silicone about 40 µm thick. FIG. 6D shows more detail. The flexible circuit includes perforated tabs 615 along is edges. Curving the flexible circuit electrode array in a solid wall would significantly reduce flexibility. The tabs 615 allow the flexible circuit electrode array to be curved up while remaining flexible. The perforated tabs 615 are embedded in the soft polymer 611 after they are curved. This both makes the flexible circuit easier to curve and improves adhesion between the flexible circuit and the soft polymer 611 by the soft polymer 611 binding to itself through holes in the perforated tabs 615. This design also allows for reduced soft polymer over mold versus the prior art, which adds flexibility. The curve up at the edges of the array 610 preferably has a radius between 0.05 mm to 0.10 mm. Too much curvature may result in sharp edges contacting the retina 15. Too little curvature may result in the tabs 615 not lifting off the surface of a small retina 15. It is important that the top of the tabs not touch the retina 15, as they may have sharp edges. The radius is preferably slightly below bottom of the tabs 615. If the bottom of the tabs 615 is at the radius the spaces between tabs 615 could produce sharp edges against the retina 15. If the bottom of the tabs 615 is too far above the radius, the resulting wall will reduce flexibility.

Figure 7A:
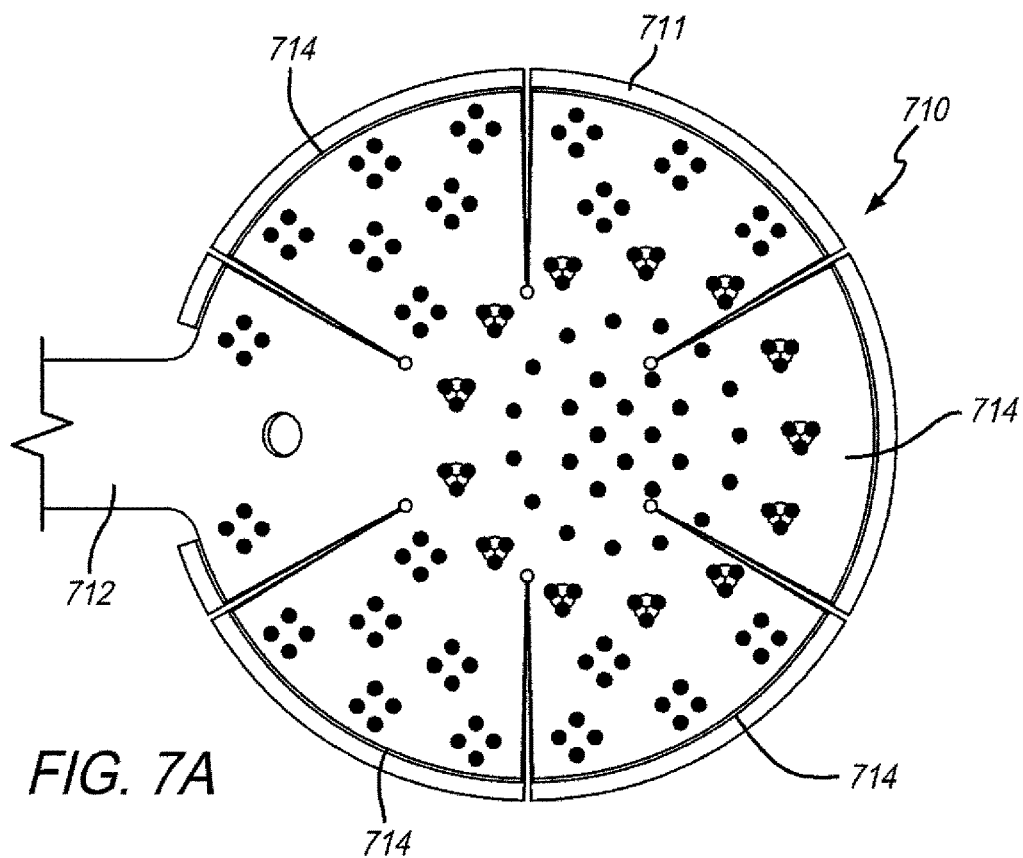
FIG. 7A shows an alternate electrode array design to provide a greater field of view.
Figure 7B:
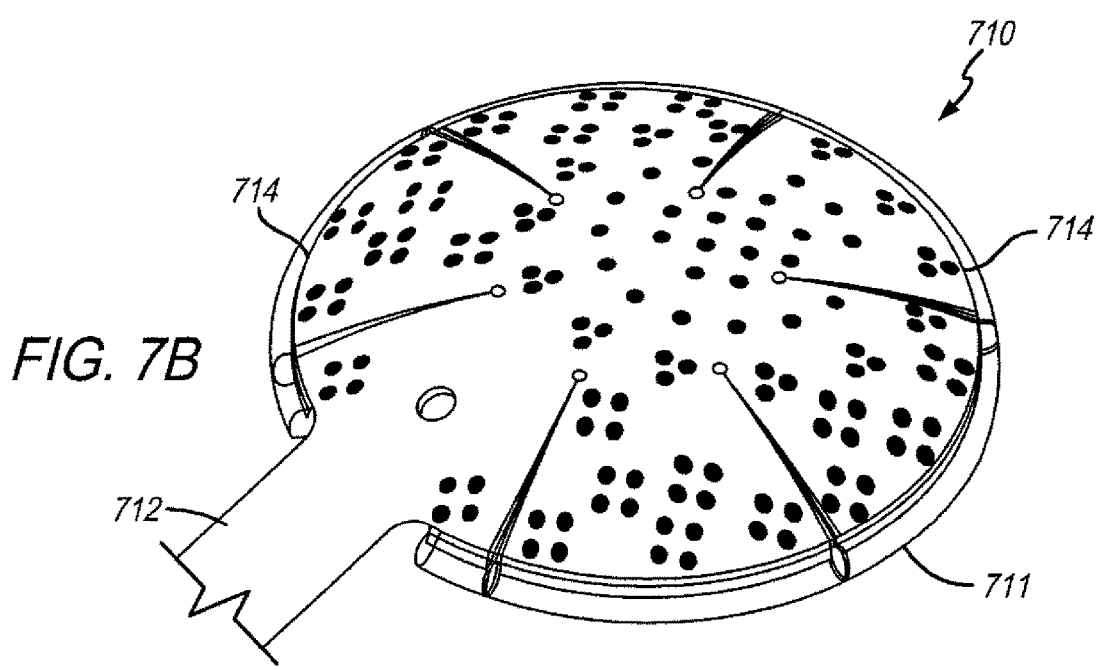
FIG. 7B shows the electrode array of FIG. 7A curved as it would be on a retina.

FIGS. 7A and 7B show an alternate embodiment for a wider field of view. As noted before, it is difficult to curve a flexible circuit to a spherical shape. The metal bond pads, traces and electrodes are patterned by photolithography, a flat process. The thin film of the flexible circuit, preferably polyimide, cannot stretch without breaking the electrical traces. To form the large electrode array 710, the flexible circuit is formed in wings 714 allowing for radial slots or spaces between the wings. Preferably the slots are in a wedge shape. The flexible circuit cable 712 exits from one wing 714. Closing the gaps between the wings 714 allows the array 710 to be curved through thermoforming into an approximately a spherical shape. The array is still coated with a softer polymer 711, preferably PDMS. The soft polymer coating 711 can hold the wings 714 together or the wings 714 can remain separate and curve when tacked to a retina through tack opening 729.

Figure 8A:
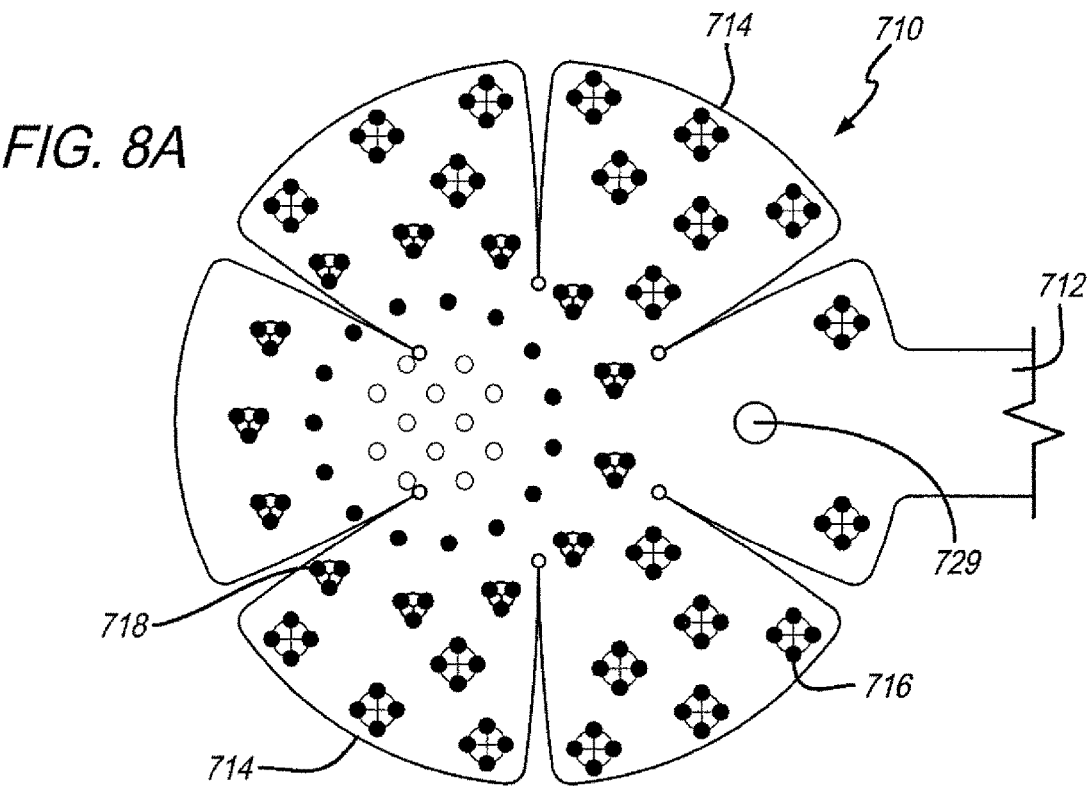
FIG. 8A shows an alternate electrode array design for a greater field of view and aggregate electrodes in its periphery, wherein the layout is symmetrical.
Figure 8B:
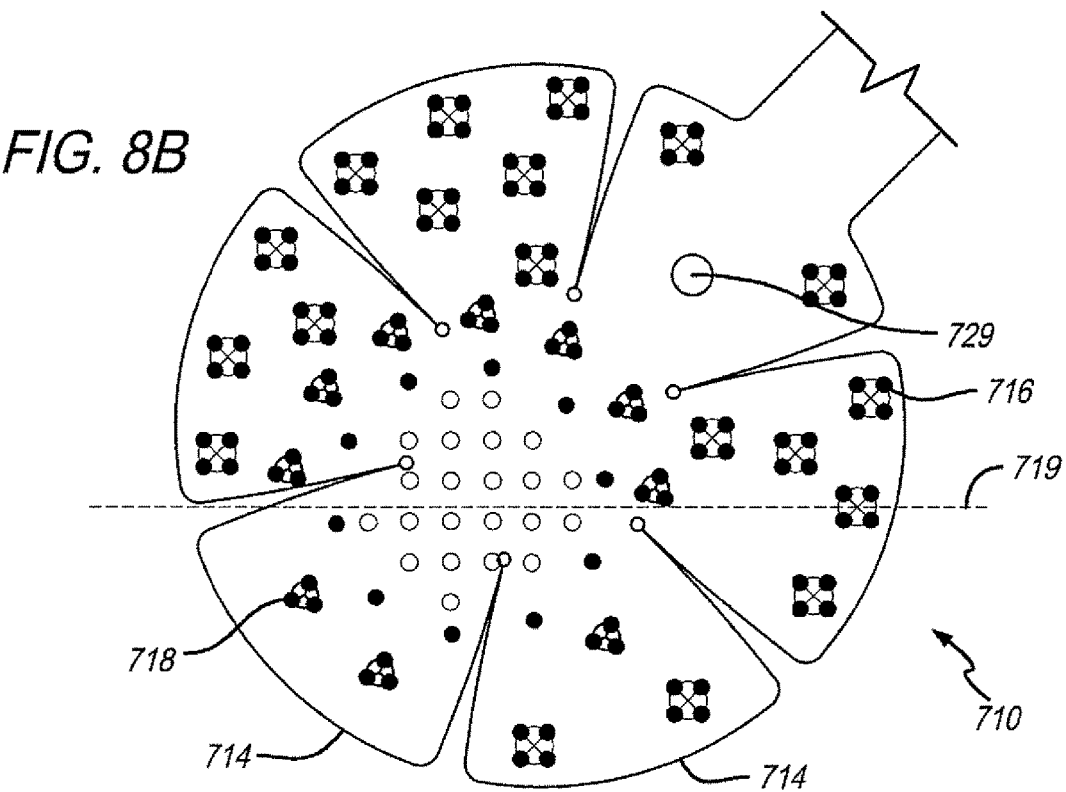
FIG. 8B shows an alternate electrode array design for a greater field of view and aggregate electrodes in the periphery, where the layout is asymmetrical with more electrodes in the lower part of the field of view.
Figure 8C:
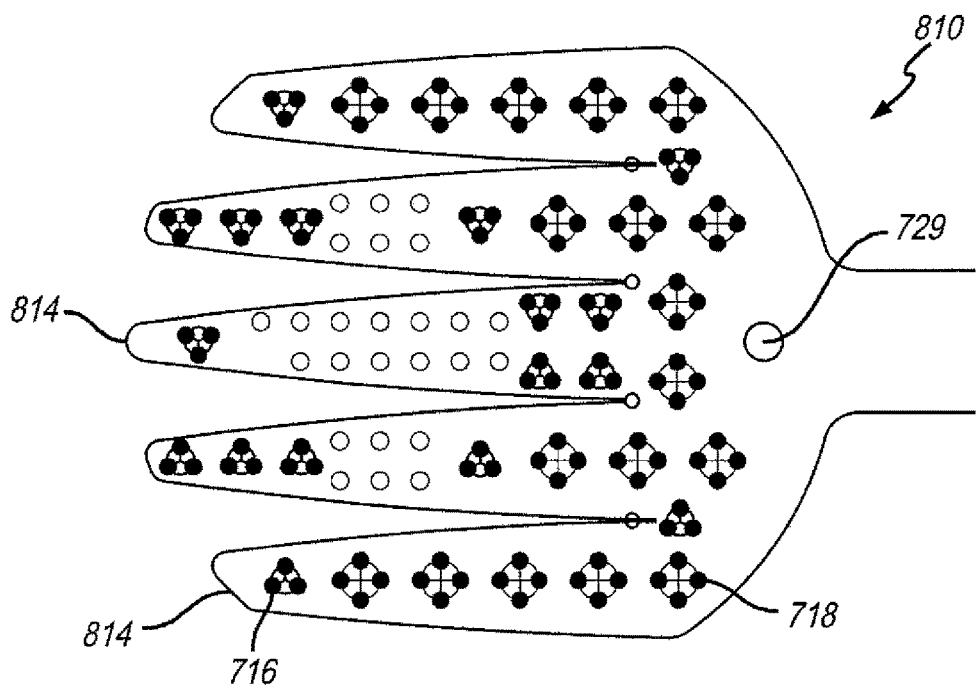
FIG. 8C shows an alternate electrode array design for greater field of view utilizing a fingered structure to increase space for electrode traces and improved array fit.

FIGS. 8A and 8B show the electrode array of FIG. 7 in greater detail, including aggregate electrodes. Neurons in the periphery of the retina produce lower resolution vision and generally require more charge to create a percept (have a higher threshold). Like FIG. 7, FIG. 8A shows an array 710 with wings 714. The electrodes in the periphery are aggregate in one pixel maps to either four electrodes 716 or three electrode 718. One of skill in the art will understand that other numbers of grouped electrodes fall within the spirit of the invention. FIG. 8A shows an array with a circular and symmetrical layout. FIG. 8B shows the array of FIG. 8A, but with asymmetrical layout. Line 719 in FIG. 8B shows the centerline of vision as the array should be implanted. This embodiment provides more electrodes above the line of central vision 719 which is below the centerline in the visual field as the lens of an eye reverses an image on the retina. People with low vision, prefer more vision in the lower part of their visional field to improve their navigational ability. FIGS. 8A through 8C additionally provide variable pitch electrodes across the array surface. Natural vision is higher resolution at the macula, center, and lower resolution in the periphery. Variable pitch electrode arrays provide more natural vision.

FIG. 8C shows another alternate embodiment. The electrode array 810 is shaped like a fork with lateral wings 814 and lateral slots in a common direction, rather than radial wings as shown in FIGS. 8A and 8B. One disadvantage of radial wings is the limit of the depth of the slots between wings. The central portion of the array must be large enough to carry all of the traces linking the electrodes to bond pads. The design of FIG. 8C allows for deeper slots between the wings 814 as the traces run laterally through an end portion. The design provides improved apposition and fit to the retina. This arrangement is more conducive to a linear array arraignment, which simplifies electrode mapping. The fork design is also easier to fold to fit through a small sclerotomy (incision in the sclera).

Figure 9A:
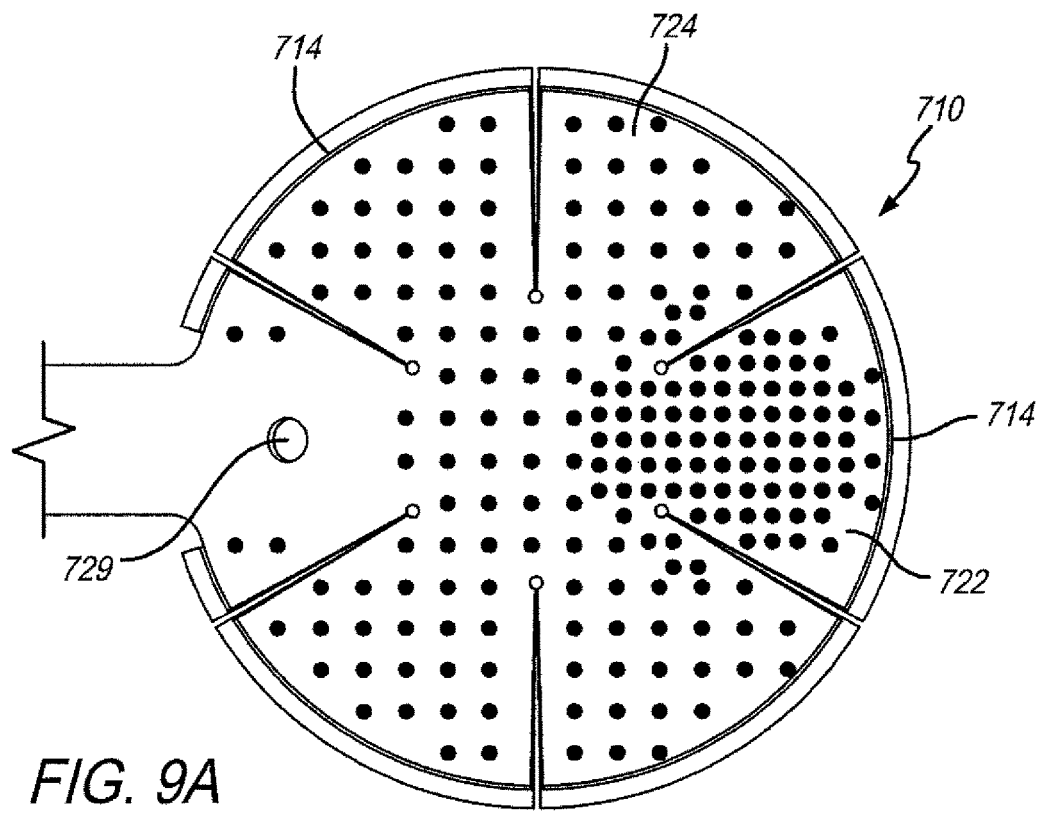
FIG. 9A shows an alternate electrode array design for a greater field of view and higher resolution.

FIGS. 9A and 9B is similar to the embodiment of FIG. 7, but provides more electrodes for higher resolution vision. Even though it is higher resolution over all, it is still advantageous to include a variable pitch with higher resolution 722 near the fovea, and lower resolution 721 in the periphery.

Figure 10:
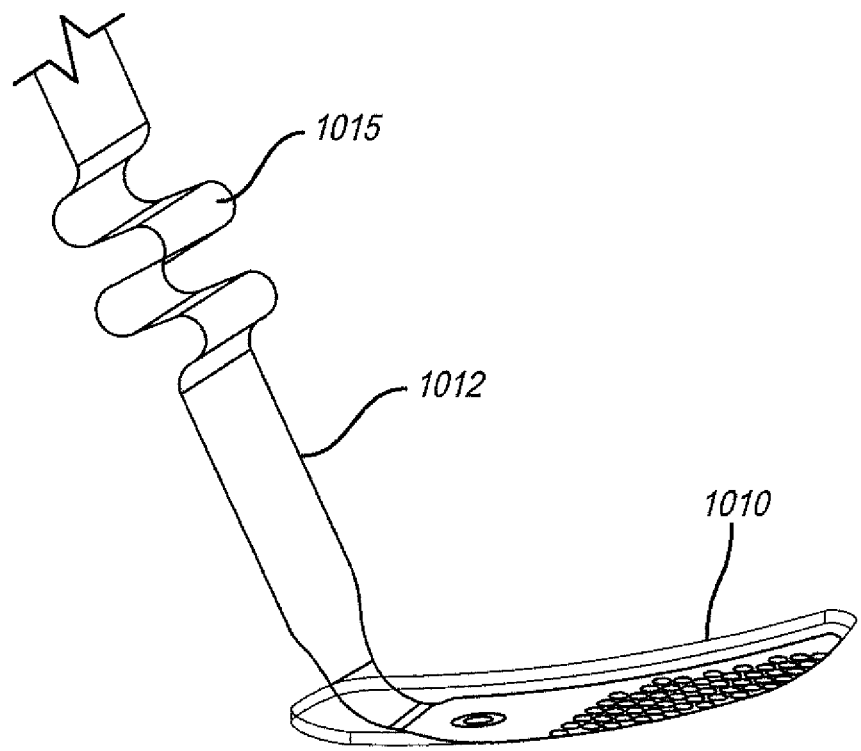
FIG. 10 shows an alternate flexible circuit cable with a stress relief feature.

FIG. 10 shows an alternate flexible circuit cable 1012. The flexible circuit cable 1012 may be used in conjunction with any of the previously described array designs 1010, but the array cable 1012 undulates to provide a stress relief feature 1015. Note than most of this disclosure is directed to the difficulty of curving a flexible circuit in a spherical shape. The undulations are cylindrical in shape and thus easier to achieve. The stress relieve feature 1015 reduces the transmission of stress from the electronics package or sclerotomy to the electrode array 1010.

A smaller electrode array is optimized for Age Related Macular Degeneration (AMD). In AMD the retina looses light sensation in the center or macula and the disease progresses outward. Patients suffering from AMD often have good peripheral vision long after the vision in the macula is completely lost. Retinitis Pigmentosa (RP) operates in almost the opposite as AMD. Vision is first lost in the periphery and the disease progresses inward. However, RP patients see less of a difference between central and peripheral vision.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:
1. An implantable device comprising:
  a base polymer layer;
  a metal layer on the base polymer layer forming electrodes in an electrode array region at a first end, bond pads in a bond pad region at a second end opposite the first end and traces connecting the electrodes to the bond pads through a cable between the electrode array region and the bond pad region;
  a top polymer layer on the base polymer layer and the metal layer and defining openings for the electrodes;
  the base polymer layer and the top polymer layer forming a plurality of perforated tabs along edges of the electrode array region;
  wherein the perforated tabs along the edges of the base polymer layer and the top polymer layer around the electrode array region are curved upward, away from the electrode openings, and embedded in a soft polymer, which is softer than the base polymer layer, and bonds to itself through perforations in the tabs, the perforated tabs allowing the edge to be curved up without reducing flexibility.

2. The implantable device according to claim 1, wherein the electrode array region defines an opening suitable to receive a tack.

3. The implantable device according to claim 1, wherein the electrode array region is curved to approximate the curvature of a retina.

4. The implantable device according to claim 1, wherein the edges are curved up with a radius of between 0.05 mm and 0.10 mm.

5. The implantable device according to claim 1, wherein the base polymer layer and top polymer layer form spaces between the tabs to facilitate curvature of the electrode array region.

* * * * *